US008921320B2

(12) United States Patent
Paul et al.

(10) Patent No.: US 8,921,320 B2
(45) Date of Patent: Dec. 30, 2014

(54) TARGETED OSMOTIC LYSIS OF CANCER CELLS

(75) Inventors: Dennis J. Paul, New Orleans, LA (US); Harry J. Gould, New Orleans, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 13/552,909

(22) Filed: Jul. 19, 2012

(65) Prior Publication Data

US 2013/0184218 A1  Jul. 18, 2013

Related U.S. Application Data

(60) Provisional application No. 61/510,258, filed on Jul. 21, 2011.

(51) Int. Cl.
| | |
|---|---|
| A61K 38/00 | (2006.01) |
| A61K 31/425 | (2006.01) |
| A61K 31/335 | (2006.01) |
| A61K 31/35 | (2006.01) |
| A61K 31/21 | (2006.01) |
| A61K 31/045 | (2006.01) |
| A61K 31/7048 | (2006.01) |
| A61K 31/704 | (2006.01) |
| A61K 31/4375 | (2006.01) |
| A61K 45/06 | (2006.01) |
| A61N 1/36 | (2006.01) |
| A61N 1/04 | (2006.01) |

(52) U.S. Cl.
CPC .......... *A61K 31/7048* (2013.01); *A61K 31/704* (2013.01); *A61K 31/4375* (2013.01); *A61K 45/06* (2013.01); *A61N 1/36* (2013.01); *A61N 1/0456* (2013.01); *A61N 1/0452* (2013.01)
USPC .......... 514/17.4; 514/171; 514/19.3; 514/216; 514/26; 514/279; 514/366; 514/450; 514/456; 514/460; 514/511; 514/521; 514/729

(58) Field of Classification Search
None
See application file for complete search history.

(56) References Cited

U.S. PATENT DOCUMENTS

| | | | | |
|---|---|---|---|---|
| 7,393,657 | B2 | 7/2008 | Diss et al. | 435/7.23 |
| 7,742,811 | B2 | 6/2010 | Schroeppel et al. | 607/3 |
| 2007/0105790 | A1 | 5/2007 | Khodadoust et al. | 514/34 |
| 2009/0018088 | A1* | 1/2009 | Valdes et al. | 514/26 |
| 2009/0074665 | A1 | 3/2009 | Diss et al. | 424/9.1 |

OTHER PUBLICATIONS

Fraser et al. 2000 "Effects of voltage-gated ion channel modulators on rat prostatic cancer cell proliferation: comparison of strongly and weakly metastatic cell lines" Prostate 44:61-76.*
Jellet et al. 1992 "Paralytic shellfish poison (saxitoxin family) bioassays: automated endpoint determination and standardization of the in vitro tissue culture bioassay, and comparison with the standard mouse bioassay" Toxicon 30(10):1143-56 (abstract only).*
Tyler et al. 2008 "Remote excitation of neuronal circuits using low-intenstiy, low-frequency ultrasound" PLOS one 3(10):e3511 pp. 1-11.*
Huang et al. 2006 "Characterization of voltage-gated sodium-channel bloackers by electrical stimulation and fluorescence detection of membrane potential" Nature Biotech 24(4):439-446.*
Hausmann et al. 2001 "Magnetic stimulation induces neuronal c-fos via tetrodotoxin-sensitive sodium channels in organotypic cortex brain slices of the rat" Neurosci Letters 310:105-108.*
Allen, D.H. et al., "Ion channel phenotype of melanoma cell lines," J. Membr. Bio, vol. 155, pp. 27-34 (1997).
Bennett, E.S. et al., "Voltage-gated Na+ channels confer invasive properties on human prostate cancer cells," Pflugers Arch., vol. 447, pp. 908-914 (2004).
Blandino, J.K. et al., "Voltage-dependent sodium channels in human small-cell lung cancer cells: role in action potentials and inhibition by Lambert-Eaton syndrome IgG," J. Membr. Biol., vol. 143, pp. 153-163 (1995).
Brackenbury, W.J. et al., "The neonatal splice variant of NaV1.5 potentiates in vitro invasive behavior of MDA-MB-231 human breast cancer cells," Breast Cancer Res. Treat., vol. 101, pp. 149-160 (2007).
Diaz, D. et al., "Functional expression of voltage-gated sodium channels in primary cultures of human cervical cancer," J. Cell. Physiol., vol. 210, pp. 469-478 (2007).
Djamgoz, M.D.A. et al., "Directional movement of rat prostate cancer cells in direct-current electric field: involvement of voltage gated Na+ channel activity," J. Cell. Sci , vol. 114, pp. 2697-2705 (2001).
Fraser, S.P. et al., "Contribution of functional voltage-gated Na+ channel expression to cell behaviors involved in the metastatic cascade in rat prostate cancer: I. Lateral motility," J. Cell Physiol., vol. 195, pp. 479-487 (2003).
Fraser, S.P. et al., "Electrophysiological effects of estrogen on voltage-gated $Na^+$ channels in human breast cancer cells," Eur. Biophys. J., vol. 36, pp. S228 (2007).

(Continued)

*Primary Examiner* — Gregory S Emch
*Assistant Examiner* — Adam M Weidner
(74) *Attorney, Agent, or Firm* — Bonnie J. Davis; John H. Runnels (57) ABSTRACT

A targeted osmotic lysis (TOL) of tumor cells that over-express voltage-gated sodium channels (VGSCs) has been developed that uses a combined therapy of a drug that blocks sodium, potassium-adenosine triphosphatase ($Na^+$, $K^+$-ATPase) that is then followed by an activation of VGSCs, for example, by electrical or pharmacological stimulation. Activation of VGSCs conducts sodium into the cancer cells in much greater amounts than non-cancer cells. Water follows this sodium gradient into the cancer cells, causing swelling and lysis. Because non-cancerous cells do not over-express VGSCs, less sodium and less water will enter the cells, and the non-cancerous cells will not lyse. This method is applicable to all cells that over-express VGSCs, including, but not limited to, highly invasive breast cancer, prostate cancer, small cell lung cancer, non-small cell lung carcinoma, lymphoma, mesothelioma, neuroblastoma, and cervical cancer.

18 Claims, 2 Drawing Sheets

(56) References Cited

OTHER PUBLICATIONS

Fraser, S.P. et al., "Tetrodotoxin suppresses morphological enhancement of the metastatic Mat-LyLu rat prostate cancer cell line," Cell Tissue Res, vol. 295, pp. 505-512 (1999).
Fraser, S.P. et al., "T-lymphocyte invasiveness: control by voltage-gated Na+ channel activity," FEBS Lett., vol. 569, pp. 191-194 (2004).
Fraser, S.P. et al., "Voltage-gated sodium channel expression and potentiation of human breast cancer metastasis," Clin. Cancer Res., vol. 11, pp. 5381-5389 (2005).
Fulgenzi, G. et al., "Human neoplastic mesothelial cells express voltage-gated sodium channels involved in cell motility," Int. J. Biochem. Cell Biol., vol. 38, pp. 1146-1159 (2006).
Gillet, I. et al., "Voltage-gated sodium channel activity promotes cysteine cathepsin-dependent invasiveness and colony growth of human cancer cells," J. Biol. Chem., vol. 284, pp. 8680-8691 (2009).
Gould HJ III et al., "Development of inflammatory hypersensitivity and the augmentation of sodium channels in rat dorsal root ganglia," Brain Res., vol. 824, pp. 296-299 (1999).
Gould HJ III et al., "Ibuprofen blocks changes in $Na_v$ 1.7 and 1.8 sodium channels associated with complete Freund's adjuvant-induced inflammation in rat," J Pain, vol. 5, pp. 270-280 (2004).
Gould HJ III et al., "Rapid sodium channel augmentation in response to inflammation induced by complete Freund's adjuvant," Brain Res., vol. 802, pp. 69-74 (1998).
Gould, H.J. III et al., "The modulation of sodium channels during inflammation," In: *The Management of Acute and Chronic Pain: the Use of the "Tools of the Trade"*. Proceedings of the Worldwide Pain Conference, San Francisco, USA, (E. Krames and E Reig, eds) Monduzzi Editore, Balogna, Italy. pp. 27-34 (2000).
Grimes, J.A. et al., "Differential expression of voltage-activated Na+ currents in two prostatic tumour cell lines: contribution to invasiveness in vitro," FEBS Lett., vol. 369, pp. 290-294 (1995).
Laniado, M.E. et al., "Expression and functional analysis of voltage-activated Na+ channels in human prostate cancer cell lines and their contribution to invasion in vitro," Am. J. Pathol., vol. 150, pp. 1213-1221 (1997).
Mycielska, M.E. et al., "Contribution of functional voltage-gated Na+ channel expression to cell behaviors involved in the metastatic cascade in rat prostate cancer: II. Secretory membrane activity," J. Cell. Physiol., vol. 195, pp. 461-469 (2003).
Mycielska, M.E. et al., "Expression of Na+-dependent citrate transport in a strongly metastatic human prostate cancer PC-3M cell line: regulation by voltage-gated Na+ channel activity," J. Physiol., vol. 563, pp. 393-408 (2005).
Nakajima, T. et al., "Eicosapentaenoic acid inhibits voltage-gated sodium channels and invasiveness in prostate cancer cells," Br. J. Pharmacol., vol. 56, pp. 420-431 (2009).
Onganer, P.U. et al., "Small-cell lung cancer (human): potentiation of endocytic membrane activity by voltage-gated Na+ channel expression in vitro," J. Membr. Biol., vol. 204, pp. 67-75 (2005).
Onkal, R. et al., "Molecular pharmacology of voltage-gated sodium channel expression in metastatic disease: Clinical potential of neonatal $Na_v1.5$ in breast cancer," Euro. J. of Pharm., vol. 625, No. 1-3, pp. 206-219 (2009).
Ou, S.W. et al., "Tetrodotoxin-resistant Na+ channels in human neuroblastoma cells are encoded by new variants of Nav1.5/SCN5A," Eur. J. NeuroSci., vol. 22, pp. 793-801 (2005).
Palmer, C.P. et al., "Single cell adhesion measuring apparatus (SCAMA): application to cancer cell lines of different metastatic potential and voltage-gated Na+ channel expression," Eur. Biophys. J., vol. 37, 359-368 (2008).
Roger, S. et al., "Involvement of a novel fast inward sodium current in the invasion capacity of a breast cancer cell line," Biochim Biophys. Acta, vol. 1616, pp. 107-111 (2003).
Roger, S. et al., "Voltage-gated sodium channels potentiate the invasive capacities of human non-small-cell lung cancer cell lines," Int. J. Biochem. Cell Biol., vol. 39, pp. 774-786 (2007).
Tufail, Y. et al., "Transcranial Pulsed Ultrasound Stimulates Intact Brain Circuits," Neuron, vol. 66, pp. 681-694 (2010).
Han, Futian, "Fast Electrical Lysis of Cells for Capillary Electrophoresis," Anal. Chem., vol. 75, pp. 3688-3696 (2003).
Jellett, Joanne F. et al., "Paralytic Shellfish Poison (Sacitoxin Family) Bioassays: Automated Endpoint Determination and Standardization of the in vitro Tissue Culture Bioassay, and Comparison with the Standard Mouse Bioassay," Toxicon, vol. 30, No. 10, pp. 1143-1156 (1992).
Roger, Sébastien et al., "Voltage-Gated Sodium Channels: New Targets in Cancer Therapy?" Curr. Pharm. Des., vol. 12, No. 28, pp. 3681-3695 (2006).
Tyler, William J. et al., "Remote Excitation of Neuronal Circuits Using Low-Intensity, Low-Frequency Ultrasound," PLoS One, vol. 3, Issue 10, pp. 1-11 (2008).
Wankerl, Katharina et al., "L-Type Voltage-Gated $Ca^{2+}$ Channels: A Single Molecular Switch for Long-Term Potentiation/Long-Term Depression-Like Plasticity and Activity-Dependent Metaplasticity in Humans," The J. of Neuroscience, vol. 30, No. 18, pp. 6197-6204 (2010).

\* cited by examiner

TARGETED OSMOTIC LYSIS OF CANCER CELLS

The benefit of the filing date of provisional U.S. application Ser. No. 61/510,258, filed Jul. 21, 2011, is claimed under 35 U.S.C. §119(e) in the United States and is claimed under applicable treaties and conventions in all countries.

TECHNICAL FIELD

This invention pertains to a method to target cancer cells that over-express voltage-gated sodium channels (VGSCs or "sodium channels") and to cause osmotic lysis of these cancer cells by initially inhibiting the sodium, potassium-adenosine triphosphatase ($Na^+$, $K^+$-ATPase or "sodium pump"), and then stimulating the VGSCs to cause sodium and water to enter the cancer cells.

BACKGROUND ART

Chemotherapy and radiotherapy of metastatic cancer, because of toxicity to both normal and abnormal tissues, present the clinician with the difficult challenge of trying to kill the neoplastic disease before killing the patient; a balance between treatment and rescue. All traditional cancer treatments are associated with toxicity, an increase in morbidity, and a reduction in quality of life that may extend far beyond the period of treatment. A major focus of current anti-neoplastic treatments is targeting treatment to the cancer cells, for example, targeting proteins expressed or over-expressed by cancer cells, but not by normal tissue.

Many invasive cancer cell types over-express voltage-gated sodium channels (VGSCs; or "sodium channels") by more than 1000-fold greater than normal cells (1, 2, 7). Cancer cells that over-express VGSCs are epithelial carcinomas that include, but are not limited to, highly invasive breast cancer (4, 10, 13, 27), prostate cancer (2, 6, 7, 8, 18, 19, 20, 21, 22, 26), small cell lung cancer (3, 23), non-small cell lung carcinoma (28), lymphoma (9), neuroblastoma (25), and cervical cancer (5). Mesothelioma which is not classified as an epithelial cancer is also known to over-express VGSCs (12). When these sodium channels are activated, $Na^+$ is conducted into the cells. In these cancers, the degree of metastasis is directly related to an increased expression of VGSCs (1, 7; see also U.S. Pat. No. 7,393,657). Physiologically, these cancer cells share certain cellular properties with normal excitable cells such as neurons and cardiac myocytes (for example, the conduction of action potentials). U.S. Pat. No. 7,393,657 discloses the use of inhibitors of VGSCs as a treatment for cancer, including breast cancer.

Of the 1.6 million people contracting epithelial cell cancer each year in the U.S., 40% are considered to be "highly invasive" and over-express VGSCs (10). These patients diagnosed with malignant/metastatic carcinomas are treated currently with major and often disfiguring surgical procedures, chemotherapy and/or radiation. More than 400,000 people die from epithelial cell carcinoma each year in the United States and an estimated 10 times that world-wide. In addition, another 1,200,000 U.S. patients diagnosed with invasive cancer are successfully treated with traditional surgery, chemotherapy and/or radiation. Breast cell carcinoma is an example of a highly invasive cancer. More than 40,000 people die from breast cell carcinoma each year in the United States and 465,000 world-wide. Greater than 90% of these deaths are due to metastasis of the primary tumor. In addition, another 170,000 U.S. women diagnosed with invasive breast cancer are successfully treated with traditional mastectomy, lumpectomy, chemotherapy and/or radiation. Of the 207,000 people contracting breast cancer each year, 40% of the cancers are considered to be "highly invasive", and over-express VGSCs (10).

The family of sodium channels named "voltage-gated sodium channels" was so designated due to the sensitivity to small changes (>40 mV) in the voltage gradient across the cellular membrane. They have also been shown to be activated by many forms of stimulation—mechanical disturbances in the membrane, ultrasound (29), magnetic fields (29), and several drugs. There are nine members of the VGSC family, with variants of many of the isoforms. They are designated $Na_v1.X$, where X represents 1-9. Subtypes are designated with a letter a, b, etc.

$Na^+$, $K^+$-ATPase is a ubiquitous transmembrane protein in animal cells, and functions to maintain an ion imbalance across the cell membrane where more charged ions are located outside of the cell, largely sodium ions, than inside. This produces an electrochemical gradient that is in homeostatic balance. When ionic imbalance shifts in the presence of a change in voltage an action potential is generated causing a transient osmotic shift toward an intracellular hypertonic state. The restoration of the sodium imbalance is an essential function performed by $Na^+$, $K^+$-ATPase. When $Na^+$, $K^+$-ATPase does not function properly, water follows sodium into the cell to restore osmotic balance thereby increasing cell volume. In normal cells this shift in cell volume is tolerated due to membrane compliance. Blocking $Na^+$, $K^+$-ATPase function can lead to a loss of cellular excitability and an increase in cellular volume. Many inhibitors are known, including the cardiac glycosides. The isozymes vary in their sensitivity to each of the cardiac glycoside drugs. More than 30 drugs have been shown to inhibit sodium pump activity. These include ouabain, digitalis and its active ingredients digoxin and digitoxin.

U.S. Patent Application Publication No. 2007/0105790 discloses the use of cardiac glycosides (e.g., ouabain and proscillaridin) either alone or in combination with other standard cancer therapeutic agents to treat pancreatic cancers by causing cell apoptosis.

U.S. Patent Application Publication No. 2009/0018088 discloses the use of cardiac glycosides, including digoxin and ouabain, to induce cell apoptosis as a treatment for cancer.

DISCLOSURE OF INVENTION

We have discovered that, in cancer cells that express excess VGSCs, if the $Na^+$, $K^+$-ATPase (sodium pump) is blocked, and then VGSCs are activated, the cells will lyse and die. The activation of the VGSCs causes $Na^+$ to be conducted into the cells, but due to the inhibition of the sodium pumps, the $Na^+$ cannot be pumped back out of the cell. Because water flows into the cell based on a $Na^+$ gradient, water flowing into the cell causes the cells that over-express $Na^+$ channels (i.e., allow more $Na^+$ into the cells) to swell and burst when membrane compliance is exceeded. Because a lesser amount of $Na^+$ enters normal cells that do not over-express VGSCs, normal tissue does not swell or lyse. We have called this two-stage treatment "Targeted Osmotic Lysis" (TOL), and have shown that this treatment is effective in treating highly invasive cancer cells. In addition, we have shown that some highly invasive cancer cells over-express $Na^+$, $K^+$-ATPase (the sodium pump) to compensate for the increase in $Na^+$ influx through the over-expressed VGSCs (unpublished; Data not shown). For example, MCF-7 breast cancer cells over-express Na$^+$, K$^+$-ATPase by 8- to 10-fold, whereas MDA-MB-231 breast cancer cells over-express Na$^+$, K$^+$-ATPase by only 2-fold.

In summary, we have demonstrated efficacy of TOL in both in vitro and in vivo models of invasive carcinoma. We have shown the usefulness of both electrical and pharmacological stimulation of the cancer cells to induce TOL. We have demonstrated TOL is effective in seven cell lines derived from four different tissue types. As little as 100-fold increase in sodium channel expression compared to normal tissue is sufficient to confer susceptibility to TOL treatment, although time-to-lysis is inversely related to extent of sodium channel expression. We have demonstrated in vivo that TOL does not affect normal tissue, even in those tissues that normally express relatively high concentrations of sodium channels. Finally, we have demonstrated that TOL can be induced using any drug or process that blocks sodium pumps.

MODES FOR CARRYING OUT THE INVENTION

We have developed a targeted osmotic lysis (TOL) of tumor cells that over-express VGSCs by a combined therapy of a drug that blocks Na$^+$, K$^+$-ATPase that is then followed by an activation of VGSCs, for example, by electrical, magnetic, ultrasound (29), or pharmacological stimulation. Activation of VGSCs conducts sodium into the cancer cells in much greater amounts than non-cancer cells. Water follows this sodium gradient into the cancer cells, causing swelling and lysis. Because non-cancerous cells do not over-express VGSCs, less sodium and less water will enter the normal cells, and the cells will not lyse.

This method is applicable to all cancer cells that over-express VGSCs. The cancers that over-express VGSCs can be identified through the literature or by assaying the cancer cells for VGSCs by methods known in the art (for example, U.S. Patent Application Publication 2009/0074665). For example, all epithelial cancer cells assayed to date have been shown to over-express VGSCs, including but not limited to, highly invasive breast cancer (4, 10, 13, 27), prostate cancer (2, 6, 7, 8, 18, 19, 20, 21, 22, 26), small cell lung cancer (3, 23), non-small cell lung carcinoma (28), lymphoma (9), neuroblastoma (25), and cervical cancer (5). Mesothelioma which is not classified as an epithelial cancer is also known to over-express VGSCs (12). Since all epithelial cancers studied to date have been shown to over-express VGSCs, other cancers that are classified as epithelial cell carcinomas are expected to over-express VGSCs, including but not limited to, gliomas, neuromas, hepatic cancer, ovarian cancer, bladder cancer, pancreatic cancer, thyroid cancer, splenic cancer, stomach cancer, cervical cancer, skin cancers, testicular cancer, renal cancer, and oral cancers.

The Na$^+$, K$^+$-ATPase blocker may be delivered to a single tumor via direct or intravenous administration, to a single organ or area via intravenous or intraluminal administration, or the entire body via intravenous, subcutaneous intramuscular or oral administration. Electrical or pharmacological stimulation of sodium channels can be delivered to a single tumor, a single organ, a section of the body, or the entire body. Theoretically, all types and subtypes of the VGSCs family should be equally susceptible to this technology. To date, the cell lines tested over-express Na$_v$1.5, Na$_v$1.5a and Na$_v$1.7, all of which mediated targeted lysis.

Examples of pharmaceutical compounds that can be used to block Na$^+$, K$^+$-ATPase are numerous. See, for example, U.S. Published Patent Applications No. 2007/0105790 and 2009/0018088. These compounds include, but are not limited to, the following: ouabain (g-Strophantin); dihydroouabain; ouabain octahydrate; ouabagenin; digoxin; digitoxin; digitalis; acetyldigitoxin; acetyldigoxin; lanatoside C; deslanoside; metildigoxin; gitoformate; oleanderin; oleandrigenin; bufotoxin; bufotalin; marinobufagenin (3,5-dihydroxy-14, 15-epoxy bufodienolide); palytoxin; oligomycins A, B, C, E, F, and G; rutamycin (oligomycin D); rutamycin B; strophanthin (g-strophanthin, Acocantherine); k-β-strophanthin; strophanthidin; k-strophanthoside; cymarin; erysimoside (cardenolide); helveticoside; peruvoside; hypothalamic Na., K.-ATPase inhibitory factorn (HIF); the aglycone of HIF; arenobufagin; cinobufagin; marinobufagin; proscillaridin; scilliroside; daigremontianin; and all other inhibitors of Na$^+$, K$^+$-ATPase, combinations and derivatives of each.

Methods to electrically stimulate tumor tissue are well known in the art (See, for example, U.S. Pat. No. 7,742,811). Some examples include, but are not limited to, the following: use of direct or alternating current (DC or AC); use of a direct application of electrodes to a tumor; use of a direct application of electrodes to an organ with multiple metastases; a transcutaneous electrical stimulation using deep muscle stimulator; a transcutaneous electrical nerve stimulation ("TENS") unit or similar; and whole-body electrical stimulation with a voltage no less than 40 mV and preferably about 1 V. In addition, magnetic fields and ultrasound have been used to stimulate nervous tissue, and sodium pumps (29).

Examples of pharmaceutical compounds that are known to increase the activity of VGSCs are known in the art. Examples include, but are not limited to, the following: veratridine; veracevine; antillatoxin (ATX); ATX II; batrachotoxin; aconitine; grayanotox; Grayanotoxin III Hemi(ethyl acetate); Antillatoxinn; Nigericin; gramicidin; α-Pompilidotoxin; β-Pompilidotoxin; Hoiamide A; brevetoxin (PbTx-2); ciguatoxins; scorpion neurotoxin; BDF 9148; DPI 201-106; TC0101029 (SCNM1); Cypermethrin; Alphamethrin; palytoxin; and all combinations and obvious derivatives of each of the above.

We expect that the Targeted Osmotic Lysis technique will: (1) increase the survival rate of patients with highly invasive tumors; (2) reduce the number of radical mastectomies and lumpectomies for breast cancer patients; (3) reduce the extent of morbidity due to treatment; (4) reduce recovery time from treatment; and (5) be applicable to all carcinomas that over-express VGSCs.

We have shown in in vivo TOL experiments described below a 30-40% survival rate in a breast cancer mouse model, and the in vitro experiments suggest a higher success rate once parameters are optimized. The limiting factor of in vivo TOL is the delivery efficiency of the inhibitor of the sodium pump to the tumor cells. In the initial pilot study, the tumors in which the tumors were highly vascularized and thus delivery of the inhibitor was more efficient were lysed following TOL treatment. In contrast, tumors with little vascularization remained viable. With further drug delivery improvement, it is believed that nearly all cancers that over-express VGSCs (e.g., 40% of all breast cancers) will be treatable with TOL, and in the case of breast cancers, mastectomies and lumpectomies should be reduced by up to 40%. This will also reduce the need for reconstructive surgery.

Targeted Osmotic Lysis is expected to have many advantages over traditional cancer therapies. Chemotherapy typically causes damage in healthy, as well as cancerous, tissue, leading to lengthy recovery and chronic morbidity. By comparison, TOL will destroy only cells that over-express VGSCs. Thus, a more selective lesion of diseased tissue is expected. This will contribute to fewer long-term adverse effects of treatment. Radiation therapy is typically directed to kill the healthy tissue surrounding the cancerous tissue. Like chemotherapy, this often leads to lengthy recovery and chronic morbidity. Because of the selectivity of TOL for cells that over-express VGSCs, there is little to no peri-neoplastic damage.

The adverse effects of chemotherapy and radiation therapy ("RT") are well documented, and treatment compliance is often problematic. We believe that TOL of carcinoma, when optimized, will require only one or two treatments, each lasting a few hours, with about a 2-5 week recovery from each. Because the adverse effects of the treatment are expected to be minimal compared with traditional therapies, treatment compliance is expected to be improved over traditional therapies.

Another current problem with chemotherapy and radiotherapy (RT) is the long term or permanent damage that results from these treatments. Chemotherapy is known to produce necrotic and demyelinating neuropathies, memory changes, sexual and fertility changes. Long-term adverse effects of RT vary widely with treatments, but are known to produce various neuropathies and chronic pain, motor deficits, and cognitive deficits, for whole-brain radiation. With TOL, fewer chronic adverse effects are expected and quality of life will be improved for most patients as compared to traditional treatments.

Recovery from chemotherapy and/or radiation therapy typically takes months. The recovery from a TOL treatment will involve the resorption of the dead tissue, and will manifest as fever and other flu-like symptoms. The degree of the fever and other symptoms will vary with the degree of metastasis and size of the tumors. The fever and joint pain can be alleviated with common analgesic-antipyretic treatments (acetaminophen, NSAIDs, etc.) Therefore, quality of life immediately after treatment will likely be greater than with traditional treatments.

Two possible adverse reactions to TOL might occur. In rats, an over-expression of $Na_v1.7$ VGSCs in dorsal root ganglia has been associated with inflammation (15, 16, 17). Thus, in patients that have major inflammatory diseases, such as rheumatoid arthritis, Krohn's disease, or infection, TOL might potentially produce damage to the peripheral nervous system. The second possibility of an adverse reaction might be the development of an autoimmune reaction to the proteins released as the cells lyse. As cancer cells lyse, there is the potential for abnormal proteins to be released that are recognized by T-cells as alien to the patient. This side effect has been noted for chemotherapeutic agents and radiation treatments that cause nonspecific lysis of cells.

One embodiment of this technology is a method to lyse metastatic tumor cells that have increased expression of VGSCs over that seen in non-tumor cells, said method comprising the following two steps: Step 1 is to administer to the tumor cells a compound that inhibits the activity of $Na^+$, $K^+$-ATPase; and Step 2 is to administer to the tumor cells a compound that increases the activity of the VGSCs. The combination of these two steps will cause the tumor cells to take up a surplus of sodium, which in turn will cause water to flow into the cells. The tumor cells will swell and eventually lyse due to the excess water.

A second embodiment of this technology is a method to lyse metastatic tumor cells that have increased expression of VGSCs over the activity seen in non-tumor cells, said method comprising the following steps: Step 1 is to administer to the tumor cells a compound that inhibits the activity of $Na^+$, $K^+$-ATPase; and Step 2 is to administer to the tumor cells an electrical stimulation to increase the activity of the VGSCs. Again, similar to above, the tumor cells will take in a surplus of sodium causing water to flow into the cells, and will swell and eventually lyse.

A third embodiment of this technology is a method to lyse metastatic tumor cells that have increased expression of VGSCs over the activity seen in non-tumor cells, said method comprising the following steps: Step 1 is to administer to the tumor cells a compound that inhibits the activity of $Na^+$, $K^+$-ATPase; and Step 2 is to administer to the tumor cells a magnetic stimulation to increase the activity of the VGSCs.

A fourth embodiment of this technology is a method to lyse metastatic tumor cells that have increased expression of VGSCs over the activity seen in non-tumor cells, said method comprising the following steps: Step 1 is to administer to the tumor cells a compound that inhibits the activity of $Na^+$, $K^+$-ATPase; and Step 2 is to administer to the tumor cells an ultrasound stimulation to increase the activity of the VGSCs.

A fifth embodiment is a method to identify metastatic tumor cells that would be lysed by the above embodiments, comprising assaying the tumor cells for the degree of expression of VGSCs and comparing the degree of expression with that from normal, non-tumor cells; wherein the metastatic tumor cells that would be lysed using the above methods would be tumor cells with a higher degree of expression for VGSCs.

EXAMPLE 1

Targeted Osmotic Lysis in Breast Cancer Cells

The effectiveness of TOL has been tested using an in vitro model for breast cancer. MDA-MB-231 breast cancer cells were cultured to complete confluency in 96-well plates. These breast cancer cells are known to over-express VGSCs by 1400-fold. These cells were exposed to Dulbecco's modified Eagle's medium (DMEM), or the cardiac glycoside drugs (known sodium pump inhibitors) ouabain (10 pM-100 nM; Sigma Chemical Co., St. Louis, Mo.) or digitoxin (100 pM-1 µM; Sigma) dissolved in DMEM for 30 min. After exposure to the sodium pump inhibitors, an electric current (0 V, 100 mV, or 1 V DC) was passed across the cells using an anode and a cathode placed touching the bottom of each well or an etched circuit in the bottom of the plate. The electric current was generated using a Grass Model SD9 stimulator (Grass Instruments, Quincy, Mass.) through platinum wire electrodes. In 6 of 24 wells that cells were exposed to ≥1 nM ouabain or ≥10 nM digoxin, and exposed to 100 mV or 1 V electric current, every cancer cell died (Data not shown).

EXAMPLE 2

Targeted Osmotic Lysis Using In Vivo Model of Cancer

As an in vivo model of cancer, MDA-MB-231 cells were suspended in matrigel and injected subcutaneously into the backs of 5 nude (J-NU) mice. Each mouse developed 0.75-1.2 cm tumors in 3-5 weeks. The mice were then injected subcutaneously with 10 mg/kg ouabain or saline. After 30 min, the mice were anesthetized with 4% isoflurane, and the tumors exposed through a small incision in the skin. An anode and a cathode were inserted into each tumor, and a train of 120 1 V DC pulses (10 msec, 2 Hz for 1 min) was delivered through the anode and cathode as discussed above. A total of 11 tumors were tested. Three tumors were from mice treated with ouabain and electrically stimulated (O-ES experimental). Of the rest, two were from a mouse treated with saline and not electrically stimulated (S-NS control), three were from mice treated with ouabain but not electrically stimulated (O-NS control), and three were from mice treated with saline and electrically stimulated (S-ES control). The electrical stimulation was repeated 15 and 30 min later. One day later, mice were sacrificed with an overdose of Nat pentobarbital, perfused with 4% buffered paraformaldehyde, and the tumors removed. The tumors were sectioned at 5 μm and stained with hematoxylin and eosin. Of the three tumors in the experimental group (the O-ES group), the tumor from one mouse showed 80% cell death after treatment. However, normal muscle taken from the base of the tumor in the same mouse showed no sign of cell death. The other two mice in the O-ES group had tumors that were not highly vascularized, and thus the ouabain could not efficiently distribute to the tumor cells. Consequently, no lysis was seen in the tumors of these two mice. None of the tumors in any of the other three treatments showed any sign of cell lysis.

EXAMPLE 3

In Vitro Targeted Osmotic Lysis of Multiple Cell Lines of Carcinoma

Initially we cultured MDA-MB-231 (ATCC, Manassas, Va., cat #HTB-26) breast cancer cells to complete confluency in 96-well plates. These cells over-express VGSCs by 100-fold. These cells were exposed to Dulbecco's modified Eagle's medium (DMEM; Invitrogen, Grand Island, N.Y.), or the cardiac glycoside drugs ouabain (10 pM-100 nM) or digoxin (100 pM-1 μM) dissolved in DMEM for 30 min. An electric current (0 V, 100 mV, or 1 V DC) was passed across the cells by means of an anode and a cathode placed touching the bottom of each well as in Example 1. In 6 of 24 wells that were exposed to ≥1 nM ouabain or ≥10 nM digoxin, all cancer cells died. Of these six wells, 1 well was exposed to 10 nM ouabain and 1 VDC, 1 was treated with 100 nM ouabain with 100 mVDC, 1 was treated with 100 nM ouabain and with 1 VDC, 2 were treated with 100 nM digoxin and with 1 VDC, and 1 treated with 1 μM digoxin and 100 mVDC.

We also used two cardiac glycoside drugs that are currently FDA-approved for clinical use, ouabain and digoxin, for in vitro lysis of multiple lines of carcinoma. To demonstrate that TOL is effective for any carcinoma that over-expresses VGSCs and that any sodium pump blocker could be used, we cultured seven cancer cell lines derived from tissue types representing four of the most common deadly cancers. Cell lines were: MDA-MB-231 (breast cancer); MCF-7 (breast cancer; ATCC# HTB-22); LNCaP (prostate cancer; ATCC# CRL-1740); DU145 (prostate cancer; ATCC# HTB-81); MCA-38 (colon cancer; from Dr. Augusto Ochoa); A549 (non-small cell lung cancer; ATCC# CCL-185); and 3LL (non-small cell lung cancer; from Dr. Augusto Ochoa, Louisiana State University, New Orleans, La.). Cells were plated in 35 mm diameter culture dishes in Dulbecco's Modified Eagle's Medium (DMEM, Gibco) supplemented with 4 mM L-glutamine, 1 mM sodium pyruvate and 10 μM insulin for 18-24 hr. Cells were then incubated for 15-45 min in 100 nM ouabain, 1 μM digoxin or no drug. A 2 V DC current, 200 pulses per second was passed across individual cells using a Grass Model SD9 stimulator (Grass Instruments, Quincy, Mass.) through platinum wire electrodes held in place with a David Kopf Instrument micromanipulator (Tarzana, Calif.), and the time to lysis was measured. Video recordings of representative experiments were prepared digitally using a Canon Vixia HFM400 camera attached to Leica DM IL microscope, and are available upon request. Mean time-to-lysis (±SEM) for each cell type and for each drug expressed in sec are presented in Table 1. As shown in Table 1, none of the controls lysed within the 5 min time limit. All of the cancer cells lysed, with the time to lysis faster for the cells with the largest known expression of VGSCs.

TABLE 1

Time to Lysis of Cultured Cancer Cells. Seven cell lines of carcinoma originating from four different cancer types were incubated in media alone or media + ouabain (100 nM) or media + digoxin (1 μM), and either stimulated or not stimulated. Time to lysis for a 5 min time period was determined by appearance of extracellular cytosol extending from the base of the cell or a visible split in the cell surface. Mean time-to-lysis ± SEM was calculated for each group and expressed in seconds. None of the cells from control conditions lysed within the 5 min time limit. Therefore, a value of 300 sec was used for all controls for statistical purposes. All drug + stimulation values were significantly different from controls ($p < .01$; 2-way ANOVA). VGSC data for the colon and lung cancer cells were not available.

|  | VGSC over-expression* | Ouabain + Stimulation (sec) | Digoxin + Stimulation (sec) | All Controls (sec) |
|---|---|---|---|---|
| Breast Cancer: |  |  |  |  |
| MDA-MB-231 | ++++ | 69.3 ± 4.82 (n = 44) | 68.39 ± 7.31 (n = 33) | 300 (n = 60) |
| MCF-7 | ++ | 170.5 ± 15.35 (n = 32) | 180.3 ± 9.07 (n = 10) | 300 (n = 56) |
| Prostate Cancer: |  |  |  |  |
| LNCaP | +++ | 143.1 ± 5.78 (n = 28) | 122.9 ± 3.13 (n = 21) | 300 (n = 32) |
| DU145 | +++ | 81.6 ± 3.96 (n = 30) | 111.3 ± 9.7 (n = 21) | 300 (n = 26) |
| Colon Cancer: |  |  |  |  |
| MCA-38 | na | 74.0 ± 1.0 (n = 2) | 122.7 ± 9.02 (n = 3) | 300 (n = 3) |
| Lung Cancer: |  |  |  |  |
| A549 | na | 149.9 ± 11.70 (n = 22) | 179.8 ± 10.82 (n = 22) | 300 (n = 18) |
| 3LL | na | 115.9 ± 3.33 (n = 31) | 163.75 ± 8.27 (n = 24) | 300 (n = 15) |

*Values from (24); + = ≥100-fold, ++ = ≥250-fold, +++ = ≥500-fold, ++++ = ≥1,000-fold over-expression of sodium channels.

EXAMPLE 4

In vitro TOL of Breast Cancer Using Pharmacological Stimulation of VGSCs

Figure 1:
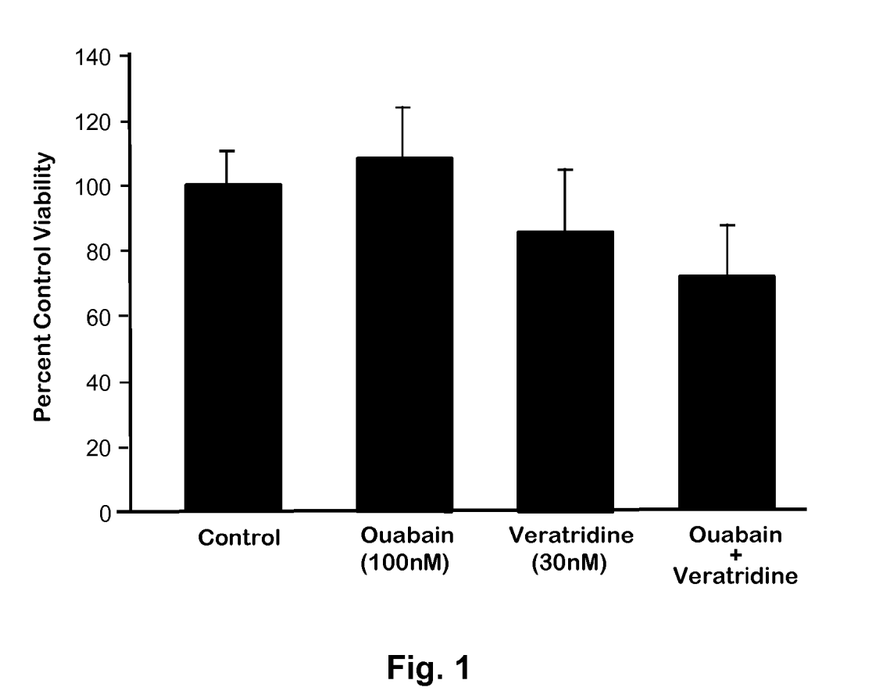
FIG. 1 illustrates the effects on cell viability of cultured breast cancer cells from a control and treatment with ouabain (a sodium pump blocker) by itself, treatment with veratridine (sodium channel stimulator) by itself, and treatment with a combination of ouabain and veratridine (Targeted Osmotic Lysis).

The effect of the combination of ouabain (a sodium pump inhibitor) and veratridine (a sodium pump stimulator) on viability of cultured MDA-MB-231 and MCF-7 breast cancer cells was assessed. The former cells over-express VGSCs by more than 1000-fold, whereas the latter cells over-express VGSCs by 100-fold (24). MDA-MB-231 cells were cultured in DMEM, whereas MCF-7 cells were cultured in DMEM+ 10 µM insulin. After centrifugation, both cell lines were resuspended in DMEM+10 µM insulin to assure normal functioning of $Na^+$, $K^+$-ATPase, and approximately 5000 cells were added to each well in a 96-well plate in a volume of 100 µl. After 18 hr, the media was aspirated, and the cells were treated with 100 µl DMEM+10 µM insulin ("media") alone, media+100 nM ouabain, media+30 µM veratridine, or media+100 nM ouabain+30 µM veratridine. After 1 hr, 10 µA alamar blue was added to each well, and cell viability determined 4 hr after this addition. All determinations were obtained in quadruplicate, and the experiment repeated three times. The results are shown in FIG. 1. In MDA-MB-231 cells, ouabain alone produced no decrease in cell viability compared to media-only controls. Veratridine alone reduced viability of MDL-MB-231 cells by 15% (FIG. 1) compared to media alone-treated cells. In this initial experiment, ouabain combined with veratridine produced a 30% reduction in cell viability. In MCF-7 cells, none of the treatments affected cell viability (Data not shown). This experiment was repeated on a 35 mm petri dish for video recording as above.

EXAMPLE 5

In Vivo Targeted Osmotic Lysis in Breast Cancer Xenographs

As an in vivo model of cancer, we injected 4 million MDA-MB-231 cells, suspended in matrigel, subcutaneously into the backs of 5 nude (J-NU) mice. Each mouse developed 0.75-1.2 cm tumors in 3-5 weeks. The mice were injected subcutaneously with 10 mg/kg ouabain or saline and then after 30 min anesthetized with 4% isoflurane. The tumors of the mice were exposed through a small incision in the skin. An anode and a cathode were inserted into each tumor, and a train of 120 1 V DC pulses (10 msec, 2 pulses per second for 1 min) using the Grass SD9 stimulator was delivered through a copper anode and cathode. Some controls received no stimulation. A total of 11 tumors were tested. Three tumors were from mice treated with 10 mg/kg s.c. ouabain and electrically stimulated (O-ES experimental). Of the rest, two tumors were from a mouse treated with saline and not electrically stimulated (S-NS control), three were from mice treated with 10 mg/kg s.c. ouabain but not electrically stimulated (O-NS control), and three were from mice treated with saline and electrically stimulated (S-ES control). The electrical stimulation was repeated 15 and 30 min later. One day later, mice were sacrificed with an overdose of $Na^+$-pentobarbital, perfused with 4% buffered paraformaldehyde, and the tumors removed. The tumors were sectioned at 5 µm and stained with hematoxylin and eosin. Of the three tumors in the experimental group (the O-ES group), the tumor from one mouse showed 80% cell death after treatment. However, normal muscle taken from the base of the tumor in the same mouse showed no sign of cell death (Photos not shown). The other two mice in the O-ES group had tumors that were not highly vascularized, and thus the ouabain could not efficiently distribute to the tumor cells. Consequently, no lysis was seen in the tumors of these two mice. None of the tumors in any of the three control treatments showed any sign of cell lysis.

This experiment was repeated using 10 mice (2 per control group and 4 in the experimental group.) Four million MDA-MB-231 cells suspended in 50% matrigel were injected s.c. in J/Nu mice, and tumors allowed to grow until visibly vascularized (reddish in appearance.) Stimulation parameters were 10 V DC, 1 msec pulses @ 200 pulses per second. Drug treatment was again 10 mg/kg s.c. ouabain. One day later, animals were sacrificed, perfused, tumors removed, and prepared for hematoxylin and eosin staining Stained sections from each of the tumors were evaluated by a trained histologist. As in the pilot experiment, none of the controls showed any sign of lysis. One control tumor showed central necrosis, which is common for fast-growing tumors. All four of the tumors treated with ouabain and electrical stimulation had an area of cell lysis that was between 50% to 80% of the total tumor volume.

To demonstrate that there is no effect of the TOL treatment on healthy, non-cancerous cells, J/Nu mice were injected with 10 mg/kg ouabain, s.c. After 30 min, muscle, peripheral nerves, heart, and brain were electrically stimulated with the parameters in the previous experiments. These tissues were selected because they have the highest normal expression of VGSCs, and would thus be expected to be most susceptible to lysis of healthy cells. One day later, the animals were sacrificed with an overdose of pentobarbital, and processed for hematoxylin and eosin staining None of these tissues showed signs of lysis.

EXAMPLE 6

Tumor Growth Following a Single TOL Treatment

Figure 2:
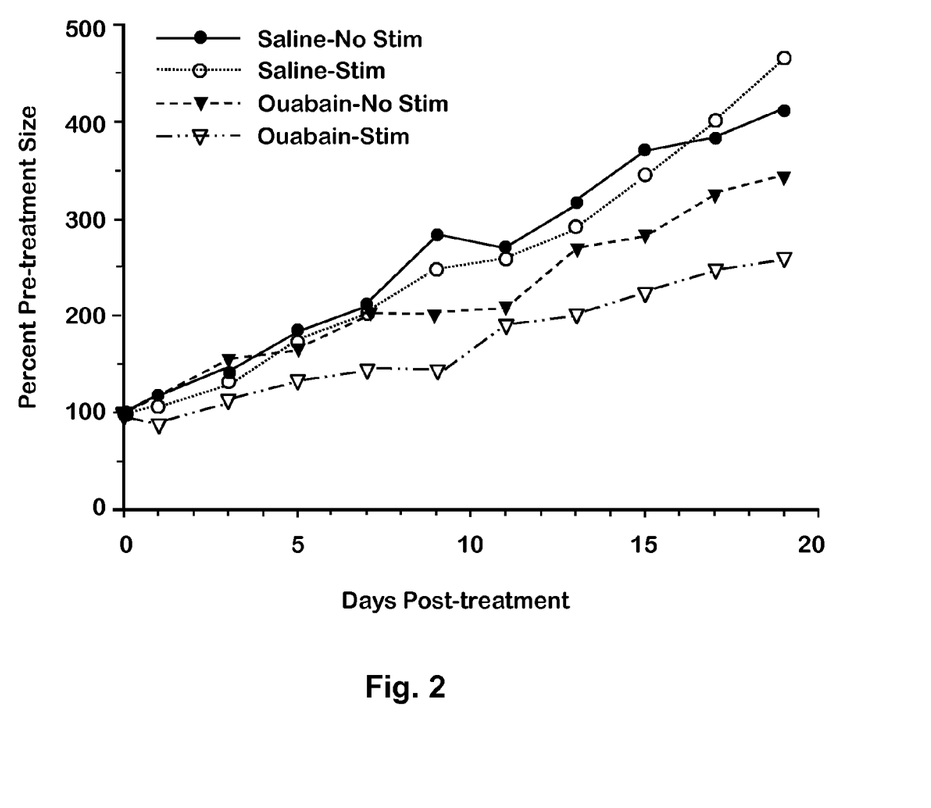
FIG. 2 illustrates the change in tumor volume over time of breast cancer xenographs in mice following a single treatment on Day 0 with saline and no electrical stimulation (Saline-No Stim), with saline and electrical stimulation (Saline-Stim), with ouabain and no stimulation (Ouabain-No Stim), or with ouabain and electrical stimulation (Ouabain-Stim).

To demonstrate an effect on post-treatment survival, 20 J/Nu mice were treated with MDA-MB-231 cells as in the previous experiment. When vascularized tumors became apparent, mice were divided into 4 treatment groups: Saline-No stimulation; Saline-Stimulation (2×1 min electrical stimulation); Ouabain (10 mg/kg)-No stimulation; and Ouabain (10 mg/kg)-Stimulation (2×1 min electrical stimulation). Only a single treatment was given for each treatment group on Day 0 of FIG. 2. Tumor cross-sectional area was then measured with calipers every-other day for three weeks. The tumor growth was expressed as a percent pre-treatment size and plotted against time. FIG. 2 shows the results of all four groups. As shown in FIG. 2, tumors on mice treated with ouabain and electrical stimulation were 70% smaller ($p<0.01$) than tumors in the three other groups.

In summary, we have demonstrated efficacy in both in vitro and in vivo models of invasive carcinoma. We have shown the usefulness of both electrical and pharmacological stimulation of the cancer cells to induce TOL. We have demonstrated TOL in seven cell lines derived from four different tissue types. As little as 100-fold increase in sodium channels expression compared to normal tissue is sufficient to confer susceptibility to TOL treatment, although time-to-lysis is inversely related to extent of sodium channel expression. We have demonstrated in vivo that TOL does not affect normal tissue, even in those tissues that normally express relatively high concentrations of sodium channels. Finally, we have demonstrated that TOL can be induced using any drug or process that blocks sodium pumps.

REFERENCES

1. Allen, D. H., Lepple-Wienhues, A., Cahalan, M. D., 1997. Ion channel phenotype of melanoma cell lines. J. Membr. Biol. 155, 27-34.
2. Bennett, E. S., Smith, B. A., Harper, J. M. (2004) Voltage-gated Na+ channels confer invasive properties on human prostate cancer cells. Pflugers Arch. 447:908-914.
3. Blandino, J. K., Viglione, M. P., Bradley, W. A., Oie, H. K., Kim, Y. I. (1995) Voltage-dependent sodium channels in human small-cell lung cancer cells: role in action potentials and inhibition by Lambert-Eaton syndrome IgG. J. Membr. Biol. 143:153-163.
4. Brackenbury, W. J., Chioni, A. M., Diss, J. K. J., Djamgoz, M. B. (2007) The neonatal splice variant of NaV1.5 potentiates in vitro invasive behavior of MDA-MB-231 human breast cancer cells. Breast Cancer Res. Treat. 101:149-160.
5. Diaz, D., Delgadillo, D. M., Hernández-Gallegos, E., Ramirez-Dominguez, M. E., Hinojosa, L. M., Ortiz, C. S., Berumen, J., Camacho, J., Gomora, J. C. (2007) Functional expression of voltage-gated sodium channels in primary cultures of human cervical cancer. J. Cell. Physiol. 210:469-478.
6. Djamgoz, M. D. A., Mycielska, M., Madeja, Z., Fraser, S. P., Korohoda, W. (2001) Directional movement of rat prostate cancer cells in direct-current electric field: involvement of voltage gated Na+ channel activity. J. Cell. Sci 114:2697-2705.
7. Fraser, S. P., Ding, Y., Liu, A., Foster, C. S., Djamgoz, M. B. (1999) Tetrodotoxin suppresses morphological enhancement of the metastatic Mat-LyLu rat prostate cancer cell line. Cell Tissue Res. 295:505-512.
8. Fraser, S. P., Salvador, V., Manning, E. A., Mizal, J., Altun, S., Raza, M., Berridge, R. J., Djamgoz, M. B. (2003) Contribution of functional voltage-gated Na+ channel expression to cell behaviors involved in the metastatic cascade in rat prostate cancer: I. Lateral motility. J. Cell Physiol. 195:479-487.
9. Fraser, S. P., Diss, J. K., Lloyd, L. J., Pani, F., Chioni, A. M., George, A. J., Djamgoz, M. B. (2004) T-lymphocyte invasiveness: control by voltage-gated Na+ channel activity. FEBS Lett. 569:191-194.
10. Fraser, S. P. Diss, J. K. J., Chioni, A. M., Mycielska, M. E., Pan H., Yamaci, R. F., Pani, F., Siwy, Z., Krakowska, m., Grzywna, Z., Brackenbury, W. J., Theodorou, D., Koyuturk, M., jiang, J., latchman, D. S., Coombes, R. C., Djamgoz, M. B. (2005) Voltage-gated sodium channel expression and potentiation of human breast cancer metastasis. Clin. Cancer Res. 11:5381-5389.
11. Fraser, S. P. Ozerlat, I., Diss, J. K. J., Djamgoz, M. B. A. (2007) Electrophysiological effects of estrogen on voltage-gated Na$^+$ channels in human breast cancer cells. Eur. Biophys. J. 36:S228.
12. Fulgenzi, G., Graciotti, L., Faronato, M., Soldovieri, M. V., Miceli, F., Amoroso, S., Annunziato, L., Procopio, A., Taglialatela, M. (2006) Human neoplastic mesothelial cells express voltage-gated sodium channels involved in cell motility. Int. J. Biochem. Cell Biol. 38:1146-1159.
13. Gillet, 1., Roger, S., Besson, P., Lecaille, G., Gore, J., Bougnoux, P., Lalmanach, G., Le Guennec, J. Y. (2009) Voltage-gated sodium channel activity promotes cysteine cathepsin-dependent invasiveness and colony growth of human cancer cells. J. Biol. Chem. 284:8680-8691.
14. Gould H J III, England J D, Liu Z P, Levinson S R (1998) Rapid sodium channel augmentation in response to inflammation induced by complete Freund's adjuvant, Brain Res. 802:69-74.
15. Gould H J III, Gould T N, England J D, Paul D, Liu Z P, Reeb S C, Levinson S R (1999) Development of inflammatory hypersensitivity and the augmentation of sodium channels in rat dorsal root ganglia, Brain Res 824:296-299.
16. Gould, H. J. III, England, J. D. and Paul, D. (2000) The modulation of sodium channels during inflammation. In: *The Management of Acute and Chronic Pain: the Use of the "Tools of the Trade"*. Proceedings of the Worldwide Pain Conference, San Francisco, USA, (E. Krames and E Reig, eds) Monduzzi Editore, Balogna, Italy. pp 27-34

17. Gould H J III, England J D, Soignier R D, Nolan P, Minor L D, Liu Z P, Levinson S R, Paul, D. (2004) Ibuprofen blocks changes in Na$_v$ 1.7 and 1.8 sodium channels associated with complete Freund's adjuvant-induced inflammation in rat. J Pain 5:270-280.
18. Grimes, J. A., Fraser, S. P., Stephens, G. J., Downing, J. E. G., Laniado, M. E., Foster, C. S., Abel, P. D., Djamgoz, M. B. (1995) Differential expression of voltage-activated Na+ currents in two prostatic tumour cell lines: contribution to invasiveness in vitro. FEBS Lett. 369:290-294.
19. Laniado, M. E., Lalani, E. N., Fraser, S. P., Grimes, J. A., Bhangal, G., Djamgoz, M. B., Abel, P. D. (1997) Expression and functional analysis of voltage-activated Na+ channels in human prostate cancer cell lines and their contribution to invasion in vitro. Am. J. Pathol. 150:1213-1221.
20. Mycielska, M. E., Fraser, S. P., Szatkowski, M., Djamgoz, M. B. (2003) Contribution of functional voltage-gated Na+ channel expression to cell behaviors involved in the metastatic cascade in rat prostate cancer: II. Secretory membrane activity. J. Cell. Physiol. 195:461-469.
21. Mycielska, M. E., Palmer, C. P., Brackenbury, W. J., Djamgoz, M. B. (2005) Expression of Na+-dependent citrate transport in a strongly metastatic human prostate cancer PC-3M cell line: regulation by voltage-gated Na+ channel activity. J. Physiol. 563:393-408.
22. Nakajima, T., Kubota, N., Tsutsumi, T., Oguri, A., Imuta, H., Jo, T., Oonuma, H., Soma, M., Meguro, K., Takano, H., Nagase, T., Nagata, T. (2009) Eicosapentaenoic acid inhibits voltage-gated sodium channels and invasiveness in prostate cancer cells. Br. J. Pharmacol. 56:420-431.
23. Onganer, P. U., Djamgoz, M. B. (2005) Small-cell lung cancer (human): potentiation of endocytic membrane activity by voltage-gated Na+ channel expression in vitro. J. Membr. Biol. 204:67-75.
24. Onkal, R., Djamgoz, M. B. A. (2009) Molecular pharmacology of voltage-gated sodium channel expression in metastatic disease: Clinical potential of neonatal Na$_v$1.5 in breast cancer.
25. Ou, S. W., Kameyama, A., Hao, L. Y., Horiuchi, M., Minobe, E., Wang, W. Y., Makita, N., Kameyama, M. (2005) Tetrodotoxin-resistant Na+ channels in human neuroblastoma cells are encoded by new variants of Nav1.5/SCN5A. Eur. J. NeuroSci. 22:793-801.
26. Palmer, C. P., Mycielska, M. E., Burcu, H., Osman, K., Collins, T., Beckerman, R., Perrett, R., Johnson, H., Aydar, E., Djamgoz, M. B., 2008. Single cell adhesion measuring apparatus (SCAMA): application to cancer cell lines of different metastatic potential and voltage-gated Na+ channel expression. Eur. Biophys. J. 37, 359-368.
27. Roger, S., Besson, P., Le Guennec, J. Y. (2003) Involvement of a novel fast inward sodium current in the invasion capacity of a breast cancer cell line. Biochim Biophys. Acta 1616:107-111.
28. Roger, S., Rollin, J., Barascu, A., Besson, P., Raynal, P. I., Iochmann, S., Lei, M., Bougnoux, P., Gruel, Y., Le Guennec, J. Y. (2007) Voltage-gated sodium channels potentiate the invasive capacities of human non-small-cell lung cancer cell lines. Int. J. Biochem. Cell Biol. 39:774-786.
29. Tufail, Y., Matyushov, A., Baldwin, N., Tauchmann, M. L., Georges, J., Yoshihiro, A., Helms Tillery, S. I., Tyler, W. J. (2010) Transcranial Pulsed Ultrasound Stimulates Intact Brain Circuits. Neuron 66:681-694.

The complete disclosures of all references cited in this specification are hereby incorporated by reference. Also incorporated by reference is the complete disclosure of the priority document, U.S. Provisional Application No. 61/510,258.

What is claimed:

1. A method for treating cancer in a mammal, said method comprising co-administering to tumor cells that over-express voltage-gated sodium channels a first agent and a second agent, wherein the first agent inhibits $Na^+$, $K^+$-ATPase, and wherein the second agent stimulates voltage-gated sodium channels; to cause the osmotic lysis of the tumor cells, resulting in a substantial reduction in tumor cell viability within about one hour after said co-administration.

2. The method of claim 1, wherein the mammal is a human.

3. The method of claim 1, wherein the tumor cells relate to a cancer selected from the group consisting of breast cancer, prostate cancer, small cell lung cancer, non-small cell lung carcinoma, lymphoma, mesothelioma, neuroblastoma, gliomas, neuromas, hepatic cancer, ovarian cancer, bladder cancer, pancreatic cancer, thyroid cancer, splenic cancer, stomach cancer, skin cancers, testicular cancer, renal cancer, oral cancers, and cervical cancer.

4. The method of claim 1, wherein the tumor cells relate to breast cancer.

5. The method of claim 1, wherein the tumor cells relate to prostate cancer.

6. The method of claim 1, wherein the tumor cells relate to colon cancer.

7. The method of claim 1, wherein the tumor cells relate to small cell lung cancer.

8. The method of claim 1, wherein the tumor cells relate to non-small cell lung cancer.

9. The method of claim 1, wherein the first agent is a drug selected from the group consisting of digoxin, digitoxin, digitalis, ouabain, oleandrin, dihydroouabain, ouabain octahydrate, ouabagenin, acetyldigitoxin, acetyldigoxin, lanatoside C, deslanoside, metildigoxin, gitoformate, oleandrigenin, bufotoxin, bufotalin, marinobufagenin, palytoxin; oligomycins, rutamycin, rutamycin B, strophanthin, k-β-strophanthin, strophanthidin, k-strophanthoside, cymarin, erysimoside (cardenolide), helveticoside, peruvoside, hypothalamic sodium, potassium-adenosine triphosphatase inhibitory factor (HIF), the aglycone of HIF, arenobufagin, cinobufagin, marinobufagin, proscillaridin, scilliroside, and daigremontianin.

10. The method of claim 1, wherein the first agent is ouabain.

11. The method of claim 1, wherein the first agent is digitoxin.

12. The method of claim 1, wherein the second agent is a stimulant selected from the group consisting of electrical current, ultrasound, magnetic field, and drug compound.

13. The method of claim 12, wherein the second agent is a drug compound selected from the group consisting of veratridine, veracevine, antillatoxin (ATX), ATX II, batrachotoxin, aconitine, grayanotox, Grayanotoxin III Hemi (ethyl acetate), Antillatoxinn, Nigericin, gramicidin, a-Pompilidotoxin, β-Pompilidotoxin, Hoiamide A, brevetoxin (PbTx-2), ciguatoxins, scorpion neurotoxin, Cypermethrin, Alphamethrin, and palytoxin.

14. The method of claim 13, wherein the drug compound is veratridine.

15. The method of claim 12, wherein the second agent is an electrical current.

16. The method of claim 12, wherein the second agent is ultrasound.

17. The method of claim 12, wherein the second agent is a magnetic field.

18. The method of claim 1, wherein non-cancerous muscle cells, non-cancerous peripheral nerve cells, non-cancerous heart cells, and non-cancerous brain cells are not osmotically lysed following said co-administration.

* * * * *